US00PP29649P3

(12) United States Plant Patent
Kordes

(10) Patent No.: US PP29,649 P3
(45) Date of Patent: Sep. 11, 2018

(54) MINIATURE ROSE PLANT NAMED 'KORPOT075'

(50) Latin Name: *Rosa hybrida*
Varietal Denomination: KORpot075

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/731,499

(22) Filed: Jun. 20, 2017

(65) Prior Publication Data

US 2017/0374771 P1 Dec. 28, 2017

Related U.S. Application Data

(60) Provisional application No. 62/493,176, filed on Jun. 23, 2016.

(51) Int. Cl.
*A01H 5/02* (2018.01)
*A01H 6/74* (2018.01)

(52) U.S. Cl.
USPC ..... Plt./119
CPC ..... *A01H 5/02* (2013.01); *A01H 6/749* (2018.05)

(58) Field of Classification Search
USPC ..... Plt./101, 116, 119
See application file for complete search history.

*Primary Examiner* — Susan McCormick Ewoldt
(74) *Attorney, Agent, or Firm* — Samuel R. McCoy, Jr.

(57) ABSTRACT

'KORpot075' is a new and distinct variety of *Rosa hybrida* which is characterized by the combination of an upright growth habit with a moderately vigorous rate of growth, very good resistance to many rose diseases, and orange double flowers borne in corymbs of 2 to 5 flowers. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination: The inventive variety of *Rosa hybrida* disclosed herein has been given the variety denomination 'KORpot075'.

STATEMENT REGARDING PRIOR DISCLOSURES BY THE INVENTOR UNDER 37 C.F.R. 1.77(B)(6)

The first public disclosure of the claimed plant, in the form of an offer for sale, was made by the wholesale nursery Rosa Danica, in Denmark, in August of 2015. In November of 2015, Rosa Danica published information pertaining to the claimed plant on their website and subsequently displayed the claimed plant at a tradeshow in Essen, Germany in January of 2016. Rosa Danica obtained the claimed plant, and all information relating thereto, from the inventor. 'KORpot075' was not publically available or sold prior to the one year anniversary of the filing date of the provisional application to which benefit is claimed.

BACKGROUND OF THE INVENTION

Parentage: 'KORpot075' is a seedling selection which resulted from the controlled pollination of an unnamed *Rosa hybrida* seedling developed and owned by the same inventor, the seed parent, and *Rosa hybrida* 'KORbailand' (U.S. Pat. No. 23,845), the pollen parent, during the summer of 2012. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2013 from the seedling beds due to its superior characteristics and asexually propagated for further evaluation. This new and distinctive rose variety was given the name 'KORpot075'.

Asexual Reproduction: The first asexual propagation of 'KORpot075', by way of softwood stem cuttings, was performed in June of 2013 at the inventor's nursery in Offenseth-Sparrieshoop, Germany. Subsequently, 'KORpot075' has been successfully propagated by stem cuttings in Jackson County, Oreg. These initial and other subsequent propagations conducted in controlled environments demonstrate that 'KORpot075' reproduces true to type in successive generations of asexual reproduction.

SUMMARY OF THE INVENTION

The following characteristics have been repeatedly observed and represent the distinguishing characteristics of the new *Rosa hybrida* cultivar 'KORpot075'. These traits, in combination, distinguish 'KORpot075' as a new and distinct cultivar.

1. *Rosa hybrida* 'KORpot075' exhibits an upright growth habit; and
2. *Rosa hybrida* 'KORpot075' exhibits moderately vigorous growth; and
3. *Rosa hybrida* 'KORpot075' exhibits very good resistance to powdery mildew and *Botrytis* diseases; and 4. *Rosa hybrida* 'KORpot075' exhibits orange flowers borne on corymbs of 2 to 5 flowers; and
5. *Rosa hybrida* 'KORpot075' exhibits medium-sized, double flowers that are held upright.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot075', taken from six month old plants.

DETAILED BOTANICAL DESCRIPTION

The following is a detailed botanical description of a new and distinct variety of *Rosa hybrida* known as 'KORpot075', based upon field observations made in May of 2017, from six month old container-grown plants in a greenhouse environment in Jackson County, Oreg. Those skilled in the art will appreciate that certain characteristics will vary with older or, conversely, with younger plants. 'KORpot075' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2001 edition except where common terms of color are used.

A botanical description of 'KORpot075' and comparisons with other varieties of *Rosa hybrida* are provided below.

General plant description:

*Growth rate.*—Moderate.

*Growth habit.*—Upright.

*Mature dimensions.*—15 cm tall and 12 cm wide, on average, when grown as a 10.5 cm nursery pot.

*Cold hardiness.*—Unknown.

*Propagation.*—Stem cuttings.

*Disease resistance.*—Very good resistance to powdery mildew (*Sphaerotheca pannosa*) and *Botrytis* diseases under normal growing conditions in Jackson County, Oreg.

Root system:

*Type.*—Fibrous root system with many root hairs.

*Branching.*—Freely branched.

*Density.*—Moderately dense rooting.

*Distribution.*—Roots distributed uniformly throughout the soil profile, from shallow to deep.

*Color.*—Greyed-Yellow Group 162D.

Stems:

*Stem color, immature stems.*—Yellow-Green Group 146C.

*Stem color, mature stems.*—Yellow-Green Group 146B.

*Anthocyanin intonations.*—Greyed-Purple Group 183B.

*Stem surface texture.*—Both immature and mature stems exhibit a smooth texture.

*Stem dimensions.*—Typical mature stems are approximately 10 cm long and 0.4 cm in diameter.

*Prickles.*—Incidence — Present; 8 to 10 prickles per 10 cm of stem, on average. Size — Average length is 3 mm. Immature prickle color — Greyed-Red Group 182B. Mature prickle color — Greyed-Purple Group 187B. Shape — Deeply concave. Texture — Smooth.

Leaves:

*Arrangement.*—Imparipinnate compound leaves; mature axillary leaves consisting of 5 leaflets.

*Attachment.*—Petiolate.

*Dimensions.*—100 mm long and 65 mm wide, on average.

*Abundance.*—Average; 30 leaves.

*Stipules.*—Size — 15 mm long and 3.0 mm wide. Stipule color — Yellow-Green Group 146C. Anthocyanin intonations — None. Stipitate glands — A limited number of stipitate glands are present along the margins. Margins — Ciliate. Texture, adaxial surfaces — Pubescent. Texture, abaxial surfaces — Glabrous. Apex — Apiculate. Base — Truncate.

*Petiole.*—Length — 20 mm. Diameter — 2.0 mm. Petiole color, adaxial surface — Yellow-Green Group 146A. Petiole color, abaxial surface — Yellow-Green Group 146A. Margins — Entire. Anthocyanin intonations — Greyed-Purple Group 187B present on the adaxial surface. Prickles — None. Stipitate glands — Limited number of stipitate glands are present on the margins, on the adaxial surface. Texture — Glabrous. Strength — Strong.

*Rachis.*—Length — Average 15 mm. Diameter — Average 1.5 mm. Color — Yellow-Green Group 146A. Anthocyanin intonations — Greyed-Purple Group 187B present on the adaxial surface at the margins and on the prickles. Margins — With stipitate glands. Prickles — A few small prickles underneath. Stipitate glands — A limited number of stipitate glands are present on the adaxial surface, at the margins.

*Leaflets.*—Quantity — Normally 5 leaflets on normal leaves in middle of the stem. Dimensions — Average size of the terminal leaflet is 35 to 40 mm long and 20 mm wide. Shape — Ovate. Apex — Acute to acuminate. Base — Obtuse. Margins — Serrulate; no undulation. Luster and texture, adaxial surface — Matte to semi-glossy, smooth and glabrous. Luster and texture, abaxial surface — Matte, leathery, and glabrous. Juvenile foliage color, adaxial surface — Green Group 137A. Juvenile foliage color, abaxial surface — Yellow-Green Group 147B. Mature foliage color, adaxial surface — Green Group 137B. Mature foliage color, abaxial surface — Yellow-Green Group 147B. Anthocyanin intonations — Greyed-Purple Group 187C present along the margins. Venation — Reticulate. Petiolule — Dimensions — 3.0 to 4.0 mm long and 1.0 mm in diameter. Petiolule color, adaxial surface — Green Group 137B. Petiolule color, abaxial surface — Yellow-Green Group 146B. Anthocyanin intonations — Greyed-Purple Group 187B are present at the margins in both juvenile and mature foliage. Prickles — None present. Texture, adaxial surface — Smooth. Texture, abaxial surface — Smooth. Margins — Smooth; occasionally with one stipitate gland.

Inflorescence:

*Inflorescence type.*—Corymbs with 2 to 5 flower buds. Flowers are held upright.

*Blooming habit.*—Continuous; prolific flowering.

*Size.*—60 mm tall and 40 mm wide, on average.

*Peduncle.*—Length — 15 to 20 mm average length. Diameter — 1.5 mm average diameter. Color — Yellow-Green Group 144A. Anthocyanin intonations — Greyed-Purple Group 184C. Strength — Strong. Texture and pubescence — Smooth; glabrous.

Flowering laterals: Present below the initiation of inflorescence. Generally 2 to 3 flowering lateral are present, with 1 to 4 flowers per flowering shoot.

Bud:

*Bud form.*—Long; pointed ovoid.

*Size.*—Upon opening, 25 mm in length from base of receptacle to distal end of bud and 12 mm diameter at its widest point.

*Texture.*—Pubescent.

*Color, as sepals first unfold.*—Yellow-Orange Group 23A.

*Color when one-quarter open, inner side.*—Marginal Zone — Orange Group N25A. Middle Zone — Orange Group N25B. Basal Zone — Yellow-Orange Group 17C.

*Color when one-quarter open, outer side.*—Red Group 46A. Marginal Zone — Orange Group 25B; veins are Yellow Group 8B. Middle Zone — Orange Group 25C; veins are Yellow Group 8B. Basal Zone — Yellow Group 8B.

*Color, outermost petals.*—Orange-Red Group 33C.

Flower:

*Blooming habit.*—Recurrent; floriferous.

*Attitude of flower.*—Flowers are held upright.

*Pedicel.*—Length — 25 mm. Diameter — 1.25 mm. Color — Yellow-Green Group 144A. Anthocyanin intonations — Greyed-Purple Group 184C. Strength — Strong. Texture — Smooth, with a few fine hairs.

*Calyx.*—General — Comprised of five polysepalous sepals, with weak foliaceous appendages present on three of the five sepals. Diameter of calyx — 14 mm, at anthesis. Sepals — Color, adaxial surface — Yellow-Green Group 144A. Color, abaxial surface — Green Group 138A. Anthocyanin intonations — Intonations of Greyed-Purple Group 183C are present on the outer surface. Size — 20 mm long and 6.0 mm wide, on average. Apex — Apiculate. Base — Flat at union with receptacle. Quantity — Five. Texture, adaxial surface — Pubescent. Texture, abaxial surface — Pubescent. Margins — Ciliate. Stipitate glands — Limited amount present on the margins of those sepals with foliaceous appendages.

*Corolla.*—Conformation — Very double. General shape of corolla — Round. Shape of corolla when viewed from the side — Upon opening, upper portion — Convex. Upon opening, lower portion — Convex. Open flower, upper portion — Convex. Open flower, lower portion — Flat. Dimensions — Medium for a miniature rose. When open, the average flower diameter is 45 to 55 mm and the average flower height is 26 to 32 mm. Fragrance — None. Duration — On the plant 16 to 20 days. Senesced petals are somewhat clinging. Petals — Petal count — 50 to 55 petals under normal conditions. Petal reflex — Somewhat reflexed. Timing of petal reflex — One by one. Petal margin — Entire. Petal shape — Deltoid. Apex — Obtuse. Base — Acute to obtuse. Dimensions — 24 to 28 mm long and 18 to 24 mm wide. Texture, inner surface — Smooth. Texture, outer surface — Smooth. Petal color, upon opening — Outermost petals, inner surface — Marginal Zone — Orange Group N25B. Middle Zone — Orange Group N25C. Basal Zone — Yellow-Orange Group 17C. Outermost petals, outer surface — Marginal Zone — Orange Group 25C. Middle Zone — Orange Group 25D. Basal Zone — Yellow Group 8C. Innermost petals, inner surface — Marginal Zone — Orange Group N25A. Middle Zone — Orange Group N25B. Basal Zone — Yellow-Orange Group 17C. Innermost petals, outer surface — Marginal Zone — Orange Group 25B; veins are Yellow Group 8B. Middle Zone — Orange Group N25C; veins are Yellow Group 8B. Basal Zone — Yellow-Orange Group 8B. Basal petal spots, upon opening — Outermost petals — Color, inner surface — Yellow Group 13A. Color, outer surface — Yellow Group 13A. Dimensions — 3.0 to 5.0 mm wide and 3.0 to 4.0 mm tall. Innermost petals — Color, inner surface — Yellow Group 13A. Color, outer surface — Yellow Group 13A. Dimensions — 3.0 to 4.0 mm wide and 2.0 to 3.0 mm tall. Petal color, after opening — Outermost petals, inner surface — Marginal Zone — Orange Group N25B, and suffused with Orange Group N25D. Middle Zone — Orange Group N25B, and suffused with Orange Group N25D. Basal Zone — Yellow Group 13A. Outermost petals, outer surface — Marginal Zone — Orange Group N25D, and suffused with Orange-Red Group 32C. Middle Zone — Orange Group N25D, and suffused with Orange-Red Group 32C. Basal Zone — Yellow Group 13A. Innermost petals, inner surface — Marginal Zone — Orange Group N25B, and suffused with Orange-Red Group 32C. Middle Zone — Orange Group N25B, and suffused with Orange-Red Group 32C. Basal Zone — Yellow Group 13A. Innermost petals, outer surface — Marginal Zone — Orange Group N25D. Middle Zone — Orange Group N25D. Basal Zone — Yellow Group 13C. Basal petal spots, after opening — Outermost petals — Color, inner surface — Yellow Group 13A. Color, outer surface — Yellow Group 13B. Dimensions — 3.0 to 5.0 mm wide and 3.0 to 4.0 mm tall. Innermost petals — Color, inner surface — Yellow Group 13A. Color, outer surface — Yellow Group 13B. Dimensions — 3.0 to 4.0 mm wide and 2.0 to 3.0 mm tall. General Tonality — Orange Group 25A. No change in general tonality at the end of the sixth day. Thereafter the general tonality is Orange Group 25B.

*Petaloids.*—Quantity — 8 to 10 petaloids per flower, on average. Dimensions — Highly variable; approximately 6.0 to 10 mm long and 3.0 to 4.0 mm wide. Color, inner surfaces — Marginal Zone — Orange Group N25A, and suffused with Yellow Group 13A. Middle Zone — Orange Group N25A, and suffused with Yellow Group 13A. Basal Zone — Yellow Group 13A. Color, outer surfaces — Marginal Zone — Orange Group N25D. Middle Zone — Orange Group N25D. Basal Zone — Yellow Group 13B. Margins — Entire; undulated. Shape — Ovate. Apex — Acute. Base — Acute to cuneate. Texture, inner and outer surfaces — Smooth.

Reproductive organs:

*Stamens.*—Quantity — Approximately 200, irregularly arranged around the styles. Anthers — Shape — Reniform. Dimensions — 2.5 mm long and 1.25 mm wide, on average. Color — Greyed-Orange Group 163C. Pollen — Absent. Filaments — Color — Yellow-Orange Group 16C, and suffused with Greyed-Red Group 179A. Length — 3.0 to 4.0 mm.

*Pistils.*—Quantity — Abundant; approximately 180. Stigmas — Dimensions — 1.0 mm long and 0.5 mm wide. Location — Equal in position to anthers. Color — Red-Purple Group 60C. Styles — Length — Variable, but generally 5.0 to 8.0 mm long. Color — Red-Purple Group 60A.

*Ovary.*—Dimensions — 2.0 to 3.0 mm long and 1.5 mm in diameter. Color — Green-White Group 156C.

*Receptacle.*—Shape — Funnel-shaped. Dimensions — Approximately 8.0 mm high and 10 mm wide. Surface — Smooth, with a few fine hairs. Color — Green Group 138A, and suffused with Greyed-Purple Group 184B.

Hips and seed formation: Not observed.

Comparisons with the parent: The new rose plant may be distinguished from its seed parent, an unnamed *Rosa hybrida* seedling, by the characteristics described in Table 1.

TABLE 1

| Characteristic | 'KORpot075' | Unnamed seed parent |
|---|---|---|
| Growth habit. | Upright. | Compact. |
| General coloration of the flower. | Orange. | Cream-yellow. |
| Shelf life as a potted plant. | Very good. | Average. |

The new rose plant may be distinguished from its pollen parent, *Rosa hybrida* 'KORbailand' (U.S. Pat. No. 23,845), by the characteristics described in Table 2.

TABLE 2

| Characteristic | 'KORpot075' | 'KORbailand' |
|---|---|---|
| Flower bud shape. | Pointed. | Globular. |
| General coloration of the flower. | Orange. | Salmon-orange. |
| Flower conformation | Double | Very double. |

Comparison with the most similar *Rosa* cultivar known to the inventor: For a comparison, several physical characteristics of the *Rosa hybrida* variety 'KORpot020', a rose variety from the same inventor which is described and illustrated in U.S. Pat. No. 23,953, are compared to 'KORpot075' in Table 3.

TABLE 3

| Characteristic | 'KORpot075' | 'KORpot020' |
|---|---|---|
| Flower size; diameter of corolla. | 45 to 55 mm. | 50 mm. |
| Petal count. | 50 to 55. | 18. |
| General coloration of the flower. | Orange Group 25A. | Orange-Red Group 33C. |

That which is claimed:

1. A new and distinct variety of rose plant named 'KORpot075', as described and illustrated herein.

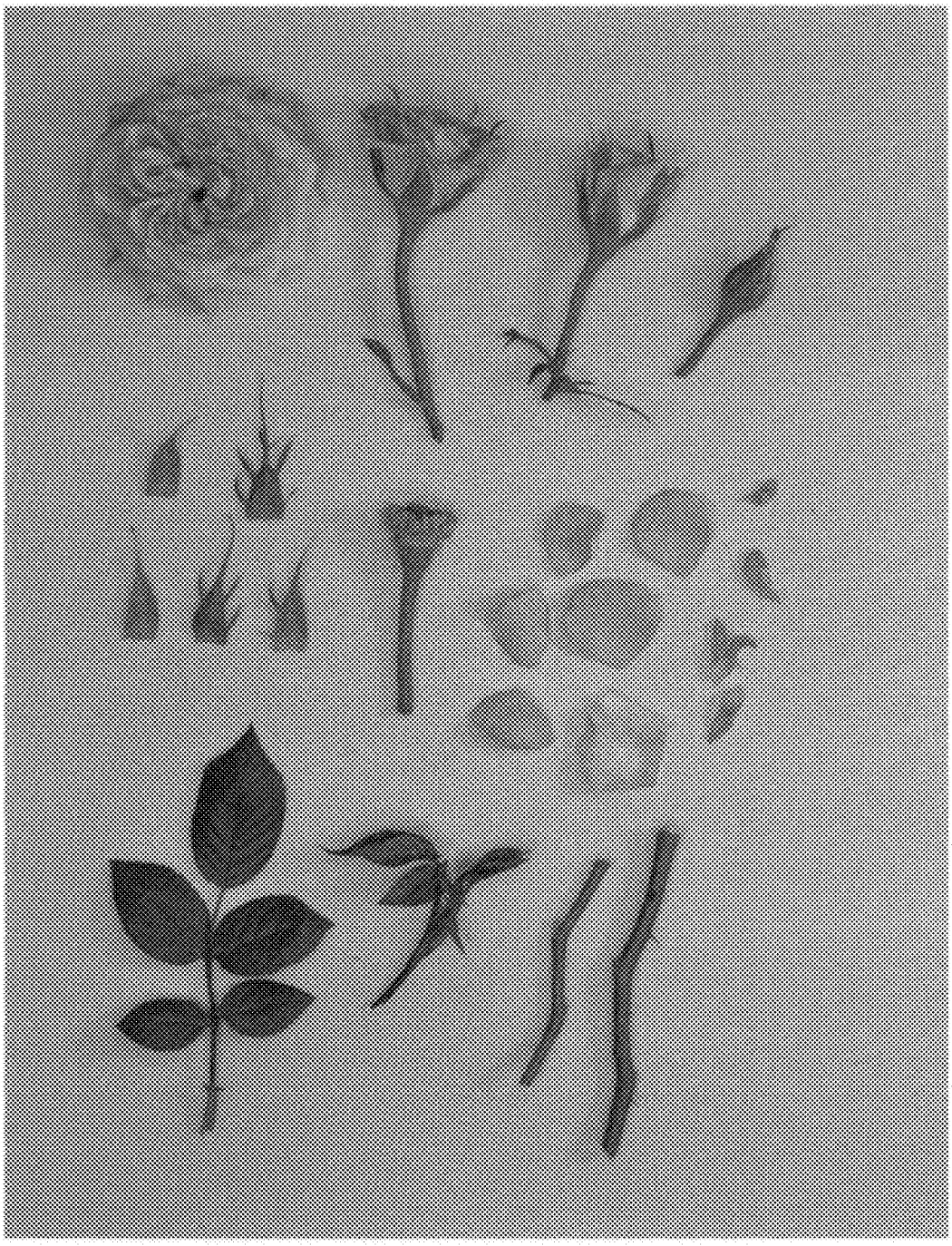

* * * * *